United States Patent [19]

Calas et al.

[11] 4,059,608

[45] Nov. 22, 1977

[54] PROCESS FOR THE PREPARATION OF HYDROGENOSILANES

[75] Inventors: Raymond Calas, Le Bouscat; Jacques Dunogues; Gérard Déléris, both of Talence; Marcel Lefort, Caluire et Cuire; Christian Simonnet, Venissieux, all of France

[73] Assignee: Rhone-Poulenc Industries, Paris, France

[21] Appl. No.: 774,486

[22] Filed: Mar. 4, 1977

[30] Foreign Application Priority Data

Mar. 5, 1976 France .............................. 76.07042

[51] Int. Cl.$^2$ ........................... C07F 7/08; C07F 7/12; C07F 7/18
[52] U.S. Cl. ....................... 260/448.2 E; 260/448.8 R; 423/324; 423/342
[58] Field of Search ................. 260/448.2 E, 448.8 R; 423/324, 342

[56] References Cited

U.S. PATENT DOCUMENTS

| | | | |
|---|---|---|---|
| 2,787,627 | 4/1957 | Kuriyagawa et al. | 260/448.2 E |
| 3,432,537 | 3/1969 | Guinet et al. | 260/448.2 E |
| 3,639,105 | 2/1972 | Atwell et al. | 260/448.2 E X |
| 3,878,234 | 4/1975 | Atwell et al. | 260/448.2 E |

*Primary Examiner*—Paul F. Shaver
*Attorney, Agent, or Firm*—Bacon & Thomas

[57] ABSTRACT

A process for preparing hydrogenosilanes by hydrogenating disilanes, especially halogenated disilanes, under relatively mild reaction conditions is disclosed. The hydrogenation is effected in the presence of a catalytic system containing an aprotic compound and a nickel catalyst which consists essentially of finely divided nickel and is obtained by preliminary or in situ reduction of a nickel compound.

10 Claims, No Drawings

PROCESS FOR THE PREPARATION OF HYDROGENOSILANES

BACKGROUND OF THE INVENTION

The present invention relates to a process for the preparation of hydrogenosilanes from disilanes.

Various processes for the preparation of hydrogenosilanes from disilanes have already been described. Thus, in Synthesis of Organosilicon Monomers (English translation published in 1964 by HEYWOOD & COMPANY, LTD), paragraph 5 of chapter XV, various methods are cited, for example, methods which use hydrochloric acid whereby the reaction is accelerated by using certain catalysts, such as the chlorides of copper, antimony and mercury, and methods which use bases such as ammonia, trimethylamine and diethylamine. This publication also mentions a method of treating residues from the direct synthesis of chlorosilanes, which allows to obtain methyl-hydrogeno-dichlorosilane by using hydrochloric acid and certain catalysts (alumina and silicic acid). Methods for treating the residues of the direct synthesis, which consists of mixtures of compounds, including, amongst others, disilanes, are described, for example, in the French Pat. No. 1,093,399, No. 2,085,143 and No. 2,163,579. However, it should be noted that the French Pat. No. 1,093,399 is essentially concerned with the scission of Si-Si, Si-O-Si or Si-C-Si bonds and the technique which is described in this patent (using hydrochloric acid and heating between 200 and 900° C) yields only a very small amount of hydrogenosilane. Likewise, in the French Pat. No. 2,163,579, according to which a disilane is reacted with a halide in the presence of platinum, or palladium, or a phosphine complex of platinum, palladium or nickel, the intention is essentially to prepare halogenosilanes containing hydrocarbon substituents and not hydrogenosilanes.

French Pat. No. 2,085,143 aims more precisely at the preparation of hydrogenochlorosilanes. According to this patent, scission of the disilanes and their hydrogenation is carried out at the same time. This operation comprises bringing the disilane into contact with gaseous hydrogen under pressure, at a temperature of between 25° and 250° C in the presence of at least 1%, by weight, relative to the disilane, of a transition metal catalyst. According to this document, this catalyst can be palladium, ruthenium, rhodium or an organophosphine complex of a transition metal, especially palladium, platinum or nickel. This process is of interest if hexamethyldisilane or monochlorinated or dichlorinated derivatives are used as starting disilane. When trichlorinated or tetrachlorinated derivatives are concerned, the technique described in the patent usually requires conditions which make industrial exploitation difficult.

SUMMARY OF THE INVENTION

It is an object of the present invention to provide a process for preparing hydrogenosilane by hydrogenation of disilanes which avoids the drawbacks of the prior art processes.

It is a further object of the present invention to provide such a process which can be effected at relatively low temperatures and under relatively low pressures.

It is a further object of this invention to provide such a process which is especially suited for hydrogenating halogenated disilanes particularly tri- or tetrachlorinated disilanes.

In order to accomplish the foregoing objects according to the present invention, there is provided a new process for preparing hydrogenosilanes which comprises the steps of contacting at least one disilane of the formula $(R)_3Si-Si(R)_3$, wherein the substituents R are alike or different and represent an alkyl group containing 1 to 6 carbon atoms, an alkoxy group containing 1 to 6 carbon atoms, phenyl, halogen, hydrogen, 3,3,3-trifluoropropyl or trimethylsiloxy, with gaseous hydrogen under pressure. This process is effected in the presence of a catalytic system consisting of:

a. 0.2 to 10%, relative to the weight of disilane, of an aprotic base, and b. 0.05 to 5%, expressed as the weight of elemental metal, relative to the weight of the disilane, of a catalyst consisting essentially of finely divided nickel obtained by reduction of a nickel compound. The nickel catalyst can be prepared in advance or in situ by reducing an inorganic or organic derivative of nickel with a reducing agent or with hydrogen.

DETAILED DESCRIPTION OF THE INVENTION

In the above formula $(R)_3Si-Si(R)_3$, the symbol R may especially represent a methyl group or a halogen atom. The disilane may be entirely halogenated, in particular, chlorinated, or may comprise, at the same time, several halogen atoms and up to 4 methyl groups, in this case the halogen atoms preferably are attached to the same silicon atom. Amongst the disilanes to which the process according to the invention applies more particularly, there may be mentioned hexachlorodisilane, dimethyltetrachlorodisilane, trimethyltrichlorodisilane and their isomers and the tetramethyldichlorosilanes, especially tetramethyl-1,1-dichlorodisilane. It must be understood that, according to the invention, it is possible to start from a mixture consisting of, in particular, two or more of the disilanes mentioned above. These various disilanes are well-known products, and in particular, the products with halogen and methyl substituents mentioned above are present in the residue from the direct synthesis of chlorosilanes by reacting methyl chloride with silicon. The aprotic base preferably are tertiary amides and may be chosen, in particular, from the group consisting of dimethylformamide, dimethylacetamide, tetramethylurea, N-methylpyrrolidone and hexamethylphosphotriamide, of which the latter is preferred.

Preferably, the quantity of aprotic base is between about 0.5 and about 5% by weight relative to the weight of the disilane or the mixture of disilanes employed in the reaction.

For preparing the nickel catalyst, and conventional reducing agent, which is able to reduce nickel into its zero valent state, can be used. Suitable reducing agents are, e.g., hydrogenosilanes, boranes or alanes (alkylhydrogen aluminium compounds).

Particularly advantageous results are obtained by using, as the nickel catalyst, the product which is obtained by the reduction of nickel chloride by a hydrogenosilane (the preparation of this catalyst is described particularly in U.S. Pat. No. 3,440,272), or of nickelocene (bis-(cyclopentadienyl)-nickel), the preparation of which is, for example, described in "Organometallic Synth. 1, 71 (1965)", the disclosure of which is hereby incorporated by reference.

The quantity of nickel catalyst preferably is from about 0.1 to about 2% by weight of nickel relative to the weight of disilane employed.

The hydrogen pressure can, for example, vary between about 5 and about 200 bars. The choice of pressure naturally depends on the nature of the disilane and its scission rate and on the reaction temperature.

As a general rule, for the silanes mentioned above, a hydrogen pressure of between about 15 and about 125 bars is advisable. The reaction temperature may be chosen from between about 50° and about 200° C; a temperature of from about 75° to about 150° C is usually preferred.

Bringing the disilane into contact with the hydrogen and the catalytic system (aprotic base and nickel catalyst) can be effected in accordance with conventional methods and using conventional equipment. In general, the disilane and the catalytic system are mixed together and then hydrogen at the chosen pressure is introduced into the reactor which is heated to the desired temperature. Recovery of the hydrogenosilane can be carried out in accordance with conventional methods.

The process according to the invention is of particular interest because it can be performed under moderate temperature and pressure conditions.

The usefulness of hydrogenosilanes is well known. There may be mentioned, for example, their use as starting reagents in the preparation of siloxanes which contain SiH-groups and which are used particularly as agents for crosslinking organopolysiloxane elastomers.

The following examples further illustrate the invention without implying a limitation thereof. In all of these examples, the indicated pressures are absolute pressures.

EXAMPLE 1

Into a 250 ml autoclave, which is swept with argon, are introduced 150 g of a chlorodisilane mixture, 81% by weight of tetrachlorodimethyldisilane, 17% by weight of trichlorotrimethyldisilane and 2% by weight of dichlorodimethyldisilane, 1.5 g of hexamethylphosphotriamide (HMPT) and 1 g of bis-(cyclopentadienyl) nickel or nickelocene.

The autoclave is closed and placed in an oven with a temperature control. Thereafter, it is purged with hydrogen, then the hydrogen pressure is fixed at 25 bars and the autoclave is heated while stirring the reagents.

At 110° C, an absorption of hydrogen is observed and when the pressure has fallen to 15 bars, it is readjusted to 25 bars. The hydrogenation is continued under these conditions for 10 minutes. The reaction is completed by raising the temperature to 150° C, whereby hydrogen pressure is kept at 25 bars (15 minutes under these conditions).

After cooling the autoclave, its contents are poured into a 250 ml flask equipped with a central stirrer, a thermometer, an argon inlet and outlet, a column containing Raschig rings (height 15 cm), an analyzer, a condenser, a 250 ml receiver and a bubble counter.

The receiver flask is cooled by means of a bath of acetone and solid carbon dioxide.

The lower-boiling products are distilled off by heating in an oil bath: boiling takes place at about 100° C. 120 g of products are distilled into the analyzer in the 35° to 75° C temperature range.

Gas phase chromatography is carried out to determine the nature and the proportion of the products obtained:

| $HSiCl_3$ | $(CH_3)_2ClSiH$ | $Cl_2CH_3SiH$ | $(CH_3)_3SiCl$ | $CH_3SiCl_3$ | $(CH_3)_2SiCl_2$ |
|---|---|---|---|---|---|
| 7.88% | 2.93% | 41.28% | 2.20% | 23.50% | 21.79% |

Thus, starting from 150 g of disilane, 120 g of monosilanes, of which 62.5 g are hydrogenosilanes, are obtained.

EXAMPLE 2

Using the same method of operation and the same quantities as in Example 1, with the exception of the hexamethylphosphotriamide (4.5 g instead of 1.5 g), 112.3 g of low-boiling products are obtained whose composition is the following:

| $HSiCl_3$ | $(CH_3)_2ClSiH$ | $Cl_2CH_3SiH$ | $(CH_3)_3SiCl$ | $CH_3SiCl_3$ | $(CH_3)_2SiCl_2$ |
|---|---|---|---|---|---|
| 4.95% | 2.81% | 40.16% | 2.23% | 24.96% | 24.87% |

EXAMPLE 3

A catalyst is used which is prepared as follows:

2 g of dry nickel chloride and 15 ml of triethylsilane are introduced into a 100 ml three-necked flask equipped with: a dropping flask, a distillation column and a mechanical stirrer. This mixture is heated to reflux and then maintained at this temperature (107° to 115° C) for 2 hours. The excess triethylsilane and triethylchlorosilane formed are distilled off and replaced with 15 ml of anhydrous decalin.

This catalyst is placed in an autoclave such as that used in Example 1 with 150 g of the mixture of disilanes used in the same example and 4.5 g of hexamethylphosphotriamide.

The operating conditions are the following: temperature 150° C and hydrogen pressure 25 bars.

114 g of a mixture of products having the following composition are recovered:

| $HSiCl_3$ | $(CH_3)_2ClSiH$ | $Cl_2CH_3SiH$ | $(CH_3)_3SiCl$ | $CH_3SiCl_3$ | $(CH_3)_2SiCl_2$ |
|---|---|---|---|---|---|
| 3.36% | 1.58% | 36.10% | 2.40% | 32.94% | 23.52% |

While the invention has now been described in terms of certain preferred embodiments, and exemplified with respect thereto, the skilled artisan will appreciate that various modifications, changes, substitutions, and omissions may be made without departing from the spirit thereof. Accordingly, it is intended that the scope of the present invention be limited solely by that of the following claims.

What is claimed is:

1. A process for preparing hydrogenosilanes, which comprises the step of contacting at least one disilane of the formula $(R)_3Si-Si(R)_3$, wherein the substituents R are the same or different from each other and represent an alkyl group containing 1 to 6 carbon atoms, an alkoxy group containing 1 to 6 carbon atoms, phenyl, halogen, hydrogen, 3,3,3-trifluoropropyl or trimethylsiloxy, with gaseous hydrogen under pressure in the presence of a catalytic system consisting essentially of:
   a. 0.2 to 10% by weight, relative to the weight of the disilane, of an aprotic base, and
   b. 0.05 to 5%, as the weight of elemental metal relative to the weight of the disilane, of a nickel catalyst which consists essentially of finely divided nickel, and is obtained by reduction of a nickel compound.

2. The process as defined in claim 1, wherein the aprotic base is a tertiary amide.

3. The process as defined in claim 2, wherein the tertiary amide is selected from the group consisting of dimethylformamide, dimethylacetamide, tetramethylurea, N-methylpyrrolidone and hexamethylphosphotriamide.

4. The process as defined in claim 1, wherein the nickel catalyst is a catalyst which is obtained by reducing the nickel compound with a reducing agent.

5. The process as defined in claim 1, wherein the nickel catalyst is a catalyst which is obtained by reducing the nickel compound with hydrogen.

6. The process as defined in claim 1, wherein the nickel catalyst is a catalyst which is obtained by reducing an inorganic nickel compound.

7. The process as defined in claim 1, wherein the nickel catalyst is a catalyst which is obtained by reducing an organic nickel compound.

8. The process as defined in claim 7, wherein the nickel compound is bis-(cyclopentadienyl) nickel.

9. The process as defined in claim 1, wherein the nickel catalyst is prepared by preliminary reduction of the nickel compound.

10. The process as defined in claim 1, wherein the nickel catalyst is prepared by in situ reduction of the nickel compound.

* * * * *